United States Patent
Kojima

(10) Patent No.: US 11,066,660 B2
(45) Date of Patent: Jul. 20, 2021

(54) TECHNIQUE FOR AGGREGATING MACROMOLECULES TOGETHER WITH CELLS

(71) Applicant: Public University Corporation Yokohama City University, Yokohama (JP)

(72) Inventor: Nobuhiko Kojima, Yokohama (JP)

(73) Assignee: PUBLIC UNIVERSITY CORPORATION YOKOHAMA CITY UNIVERSITY, Yokohama (JP)

( * ) Notice: Subject to any disclaimer, the term of this patent is extended or adjusted under 35 U.S.C. 154(b) by 884 days.

(21) Appl. No.: 15/573,765

(22) PCT Filed: May 12, 2016

(86) PCT No.: PCT/JP2016/064167
§ 371 (c)(1),
(2) Date: Nov. 13, 2017

(87) PCT Pub. No.: WO2016/182022
PCT Pub. Date: Nov. 17, 2016

(65) Prior Publication Data
US 2018/0148707 A1 May 31, 2018

(30) Foreign Application Priority Data

May 14, 2015 (JP) .............................. JP2015-099064

(51) Int. Cl.
*C12N 11/04* (2006.01)
*C12N 11/08* (2020.01)
*C12N 5/071* (2010.01)

(52) U.S. Cl.
CPC ............ *C12N 11/04* (2013.01); *C12N 5/0671* (2013.01); *C12N 11/08* (2013.01); *C12N 2513/00* (2013.01); *C12N 2533/40* (2013.01)

(58) Field of Classification Search
CPC .. C12N 11/04; C12N 5/0671; C12N 2513/00; C12N 11/08
See application file for complete search history.

(56) References Cited

FOREIGN PATENT DOCUMENTS

EP      0 258 441 A1    3/1988
JP      62-175172 A     7/1987

OTHER PUBLICATIONS

English translation of Written Opinion dated Nov. 16, 2017, in PCT International Application No. PCT/JP2016/064167.
International Search Report for PCT/JP2016/064167 (PCT/ISA/210) dated Jul. 19. 2016.
Kojima, "Fabrication of a microchannel network in multicellular spheroids by embedding hydrogel beads", Regenerative Medicine, 2013, p. 85.
Kojima et al., "Rapid aggregation of heterogeneous cells and multiple-sized microspheres in methylcellulose medium", Biomaterials, 2012, vol. 33, pp. 4508-4514.
Tsuda et al., "Bead Technology for Easy Handling of Biomaterials", Bio Industry, Dec. 12, 2009, vol. 26, No. 12, pp. 38-43.
Written Opinion of the International Searching Authority for PCT/JP2016/064167 (PCT/ISA/237) dated Jul. 19, 2016.

*Primary Examiner* — Teresa E Knight
(74) *Attorney, Agent, or Firm* — Birch, Stewart, Kolasch & Birch, LLP

(57) ABSTRACT

The present invention provides a technique for efficiently aggregating a polymer such as ECM together with cells. A method for preparing a polymer-loaded cell or cell aggregate, comprising adding a solution containing a polymer and at least one cell to a medium containing a swellable material to thereby aggregate the polymer together with the cell. A method for controlling the property and/or the function of a cell or a cell aggregate, comprising culturing the polymer-loaded cell or cell aggregate prepared by the above-described method. A method for culturing a cell or a cell aggregate, comprising: preparing a polymer capsule filled with a cell or a cell aggregate by adding a solution containing a polymer and at least one cell to a medium containing a swellable material to thereby aggregate the polymer together with the cell; and culturing the cell or cell aggregate within the capsule.
For constructing 3D cell tissues, a method using U-bottom 96-well plates or the hanging-drop method is conventionally used. In the present invention, 2000 cells can be mixed with 1 μl of ECM-containing medium so that ECM and the cells are allowed to aggregate simultaneously. When the efficiency in this case is taken as 1, ECM can only be mixed in 3D cell tissues at a calculated efficiency of approx. $\frac{1}{12000}$ in the method using U-bottom 96-well plates or approx. $\frac{1}{2400}$ in the hanging drop method. Therefore, according to the present invention, it is possible to reduce the cost of ECM can be reduced to about several thousand to ten thousand times less. Besides, it is possible to efficiently use artificial ECM that cannot be synthesized in a large quantity or rare ECM that can only be extracted in an extremely small quantity for such a reason that the source is a small organism.

10 Claims, 10 Drawing Sheets

(9 of 10 Drawing Sheet(s) Filed in Color)

Green: viable cell, Red: dead cell

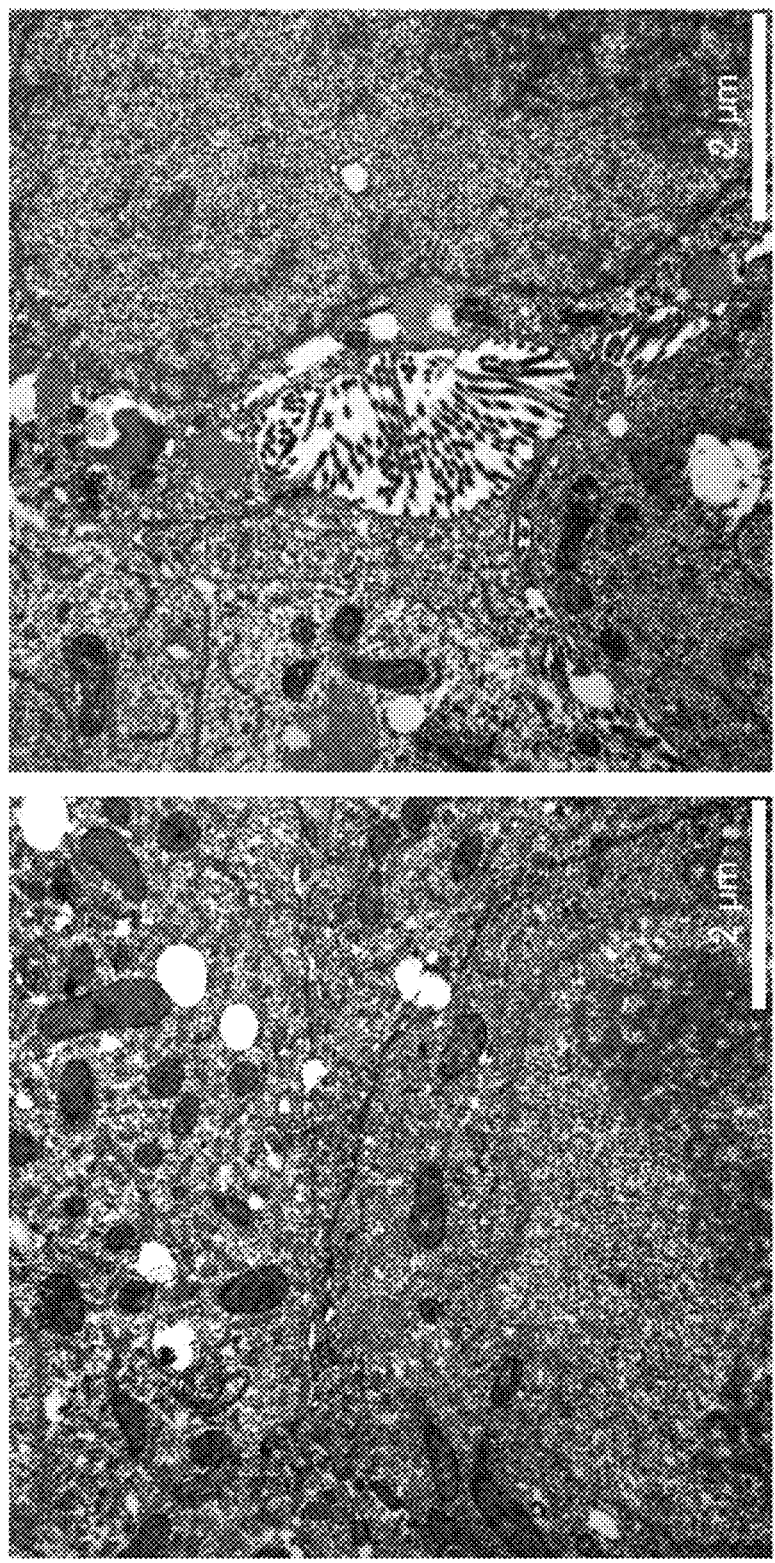

TECHNIQUE FOR AGGREGATING MACROMOLECULES TOGETHER WITH CELLS

TECHNICAL FIELD

The present invention relates to a technique for aggregating a polymer together with cells. More specifically, the present invention relates to a technique for loading a polymer between cells or a technique for filling cells into polymer capsules.

BACKGROUND ART

In cell assays or regenerative medicine using cells, it is believed that three-dimensional (3D) organization of those cells is an effective means to enhance the differentiation potential of the cells. In conventional 3D organization, non-adhesive plates or the hanging-drop method is used for preparing cell aggregates (Lin et al., Biotechnology Journal, 2008, 3, 1172-1184: Non-Patent Document No. 1). However, in order to prepare still higher value-added 3D tissues that are needed in drug screening or regenerative medicine, a more elaborate technique for constructing 3D tissues is demanded.

Organs existing in human bodies are made of cells and extracellular matrixes which are laminated in layers. To date, a technique has been reported in which fibronectin (an extracellular matrix (ECM)) and gelatin are coated on cell surfaces and the resultant cells are assembled as a lamination (Nishiguchi et al., Advanced Materials, 2011, 23, 3506-3510: Non-Patent Document No. 2; Matsusaki et al., Angewandte Chemie 2007, 46, 4689-4692: Non-Patent Document No. 3)

PRIOR ART LITERATURE

Non-Patent Documents

Non-Patent Document No. 1: Lin et al., Biotechnology Journal, 2008, 3, 1172-1184
Non-Patent Document No. 2: Nishiguchi et al., Advanced Materials, 2011, 23, 3506-3510
Non-Patent Document No. 3: Matsusaki et al., Angewandte Chemie 2007, 46, 4689-4692

SUMMARY OF THE INVENTION

Problem for Solution by the Invention

In the preparation of 3D cell tissues, a method using U-bottom 96-well plates or the hanging-drop method is conventionally used. It is possible to mix ECM into the inside of cell tissues by these methods but in contrast with 3D cell tissues which are formed as a result of the gathering of cells at the bottoms of U-bottom plates or liquid drops, ECM which is soluble is present uniformly in liquid culture media. Therefore, the most part of ECM is unable to contribute to cell aggregation.

The above-described technique for coating fibronectin and gelatin on cell surfaces and assembling the resultant cells is mainly focused at laminating cells. Further, since this technique depends on the interaction of integrin molecules on cell surface with fibronectin, it is not possible to coat all polymers on cell surfaces.

There is also a demand for filling cells into ECM gel capsules and culturing the cells therein. In conventional methods, cell-containing ECM solution is mixed with oil, followed by gelation of the resultant mixture. Such methods have a problem of cytotoxicity caused by the effect of oil.

It is an object of the present invention to provide a technique for efficiently aggregating cells together with ECM to overcome the drawbacks of conventional methods.

Means to Solve the Problem

Given a polymer solution of relatively high concentration (Polymer Solution A; e.g., liquid culture medium containing 3% methylcellulose), the present inventor found that when of a polymer solution of relatively low concentration (Polymer Solution B; e.g., Matrigel™) was injected in a small amount, the moisture content of Polymer Solution B was absorbed by Polymer Solution A (to cause its swelling) and the polymer molecules dispersed in Polymer Solution B accumulated in a smaller space than when they initially were. The present inventor paid attention to this phenomenon and decided to take advantage of it. When Polymer Solution B in which desired cells are suspended is injected into Polymer Solution A, the polymer molecules dispersed in Polymer Solution B aggregate together with the cells (FIG. 8). As a result, an aggregate is formed in which the polymer in Polymer Solution B is loaded between cells. When Polymer Solution B is gelatable and has a high concentration, the polymer derived from Polymer Solution B provides a hydrogel to form a relatively thick layer between cells. In this case, when the cell number is small relative to the liquid volume of Polymer Solution B, cell-containing capsules are formed. When the concentration of Polymer Solution B is low, the polymer derived from Polymer Solution B forms a thin coating-like layer between cells. The present invention has been achieved based on these findings. A summary of the present invention is as described below.

(1) A method for preparing a polymer-loaded cell or cell aggregate, comprising adding a solution containing a polymer and at least one cell to a medium containing a swellable material to thereby aggregate the polymer together with the cell.

(2) The method of (1) above, wherein the cell aggregate forms a three-dimensional (3D) tissue.

(3) The method of (2) above, wherein the property and/or the function of the 3D tissue is improved relative to the property and/or the function of cells that have not formed a 3D tissue or the property and/or the function of a 3D tissue that has been formed without loading a polymer between cells.

(4) The method of any one of (1) to (3) above, wherein the polymer-loaded cell or cell aggregate is a polymer capsule filled with a cell or a cell aggregate.

(5) The method of any one of (1) to (4) above, wherein the at least one cell contained in the solution to be added to the medium containing a swellable material is the polymer-loaded cell or cell aggregate prepared by the method of any one of (1) to (4) above.

(6) A method for controlling the property and/or the function of a cell or a cell aggregate, comprising culturing the polymer-loaded cell or cell aggregate prepared by the method of any one of (1) to (5) above.

(7) A method for culturing a cell or a cell aggregate, comprising:
  preparing a polymer capsule filled with a cell or a cell aggregate by adding a solution containing a polymer and at least one cell to a medium containing a swellable material to thereby aggregate the polymer together with the cell; and
  culturing the cell or cell aggregate within the capsule.

The method of the present invention is different from conventional methods in the following points: irrespective of its bonding strength to integrin, a polymer such as ECM can be loaded between cells which contribute to aggregation; and when a gelatable polymer such as ECM is used, gel in the form of a liquid drop can be formed without using oil.

Effect of the Invention

According to the present invention, it has become possible to efficiently aggregate a polymer such as ECM together with cell(s).

The present specification encompasses the contents disclosed in the specification and/or the drawings of Japanese Patent Application No. 2015-99064 based on which the present application claims priority.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 10 shows enhanced formation of bile canalicular structures by the loading of gel.

MODES FOR CARRYING OUT THE INVENTION

Figure 1:
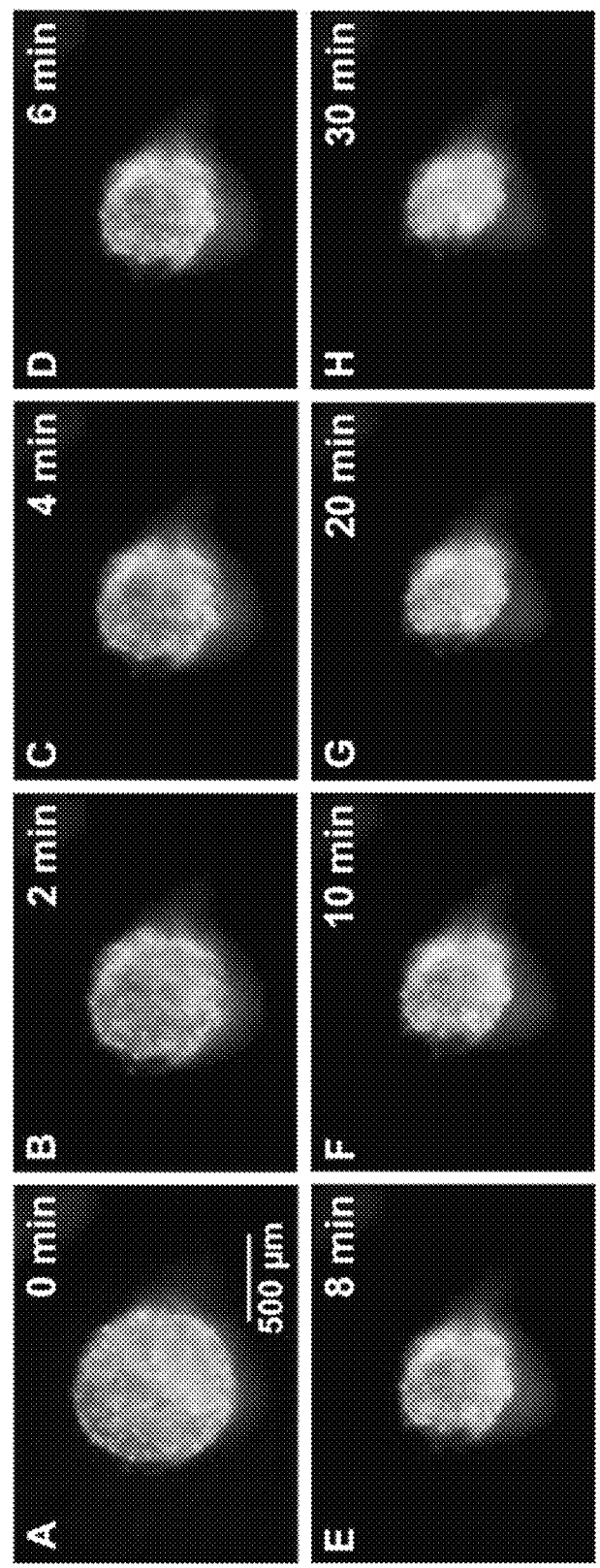
FIG. 1 shows how ECM and cells aggregate simultaneously.

Hereinbelow, the present invention will be described in more detail.

The present invention provides a method for preparing a polymer-loaded cell or cell aggregate, comprising adding a solution containing a polymer and at least one cell to a medium containing a swellable material to thereby aggregate the polymer together with the cell.

The swellable material may be any material that tends to swell upon absorption of a liquid such as water. Specific examples of swellable materials include, but are not limited to, polymers such as methylcellulose, pectin or carboxymethylcellulose.

As the medium, DMEM, αMEM or any other type of conventional medium may be used.

The polymer is not particularly limited but preferably water-soluble. Specific examples of polymers include, but are not limited to, extracellular matrix (ECM) components such as collagen (type I, type II, type IV, etc.), proteoglycans (chondroitin sulfate proteoglycan, heparan sulfate proteoglycan, keratan sulfate proteoglycans, dermatan sulfate proteoglycans), hyaluronic acid (a type of glycosaminoglycan), laminin, tenascin, entactin, elastin, fibrillin or fibronectin; organism-derived high molecular weight polysaccharides not contained in ECM, such as dextran, starch, glycogen, cellulose or alginic acid; substances derived from the above-listed substances, such as collagen-denatured gelatin; and various natural or artificial polymeric compounds. For filling a cell or a cell aggregate into a polymer capsule, the polymer is preferably gelatable. Specific examples of gelatable polymers include, but are not limited to, the above-listed ECM components and gelatin. Matrigel™ is a commercial ECM gel which contains laminin, collagen IV and entactin as ECM components and may also contain growth factors such as bFGF, EGF, IGF-1, PDGF, NGF or TGF-β. In Examples described later, growth factor reduced Matrigel™ was used with the least possible contents of growth factors such as bFGF, EGF, IGF-1, PDGF, NGF or TGF-β. When growth factor reduced Matrigel™ is used, the effect of gel components alone can be evaluated or, alternatively, other growth factors may be added afterward and checked for their effect (Reference source web page http://catalog2.corning.com/LifeSciences/ja-JP/Shopping/ProductDetails.aspx?categoryname=&productid=356231 (Lifesciences)).

The cell is not particularly limited; it may be any cell, e.g., hepatocytes, bile duct epithelial cells, α, β, δ or PP cells constituting pancreatic islets, adipocytes, bone marrow cells [the so-called hemocytes (parenchymal cells) such as leukocytes and erythrocytes, progenitor cells thereof and hematopoietic stem cells, as well as vascular endothelial cells, adipocytes, reticular cells, adventitial reticular cells, endosteal cells, osteoblasts and the like which are cells that constitute hematopoietic niche], spermatogonia, egg cells, nerve cells, osteoblasts/osteoclasts, chondrocytes, various renal tubular epithelial cells, alveolar epithelial cells, mesenchymal stem cells, ES cells and iPS cells may be enumerated.

The cell may be a single cell (e.g., egg) or a plurality of cells (cell population) may be used. Further, the cell may be allogeneic or a mixture of xenogeneic cells may be used. Still further, cells may have formed a cell aggregate. The term "cell aggregate" as used herein refers to a state in which individual cells bind together and it is a concept encompassing a 3D tissue (i.e., a plurality of cells gather three-dimensionally to adhere to each other), a spheroid, and an organoid. Further, the cell may be embedded in a gel such as alginate gel.

The cell may be either derived from nature or genetically engineered. ES cells or iPS cells, and various progenitor or mature cells differentiation-induced therefrom may also be used.

The solution to contain a polymer and at least one cell may be exemplified by, but not limited to, DMEM medium and the like.

Aggregation of a polymer together with a cell(s) may be performed under such conditions that the polymer and the cell are forcibly brought into an aggregated state in the presence of a swellable material and held in that state.

Factors that affect the degree of aggregation of cells and polymers may include, but are not limited to, the type, properties (molecular weight, etc.) and concentration of the swellable material used; the type, properties and count of the cell used; and the type, properties (molecular weight, capacity of gelation, etc.) and concentration of the polymer used. When culture is to be performed by infusing a liquid containing a polymer and cells into a medium containing a swellable material, the degree of aggregation could also be affected by such factors as the volume of the liquid, the method of its infusion, and the shape of liquid drops after infusion.

The concentration of a swellable material in the medium may be selected at a suitable value since the proper concentration may vary with the type and properties of the swellable material used. When the concentration is extremely low, sinking of 3D cell tissues in the bottom and other problems will occur. Therefore, the concentration should not be decreased below a specific level (e.g., 1% by mass when methylcellulose is used). The higher the concentration of the swellable material, the faster the aggregation speed and the greater the driving force for aggregation. However, if the concentration is too high, it then becomes difficult to disperse the swellable material in the medium and the viscosity of the medium is so high that it becomes very difficult to handle. Therefore, the concentration should not be raised beyond a specific level (e.g., 3% by mass in the case of methylcellulose). When methylcellulose is used as a swellable material, the methylcellulose concentration in the medium may preferably be 1-3% by mass. The cell count in a cell suspension (infusion) that contains a desired concentration of a polymer and which is to be injected into the methylcellulose medium may be appropriately adjusted from one cell (lower limit) to approx. 100000 cells (upper limit) per μl depending on the purpose. Spherical capsules or 3D cell tissues can be constructed by injecting the cell suspension into the methylcellulose-containing DMEM medium with a micropipette in portions of 1 μl (adjustable within a range of 0.1-10 μl) at appropriate intervals. The volume of methylcellulose-containing DMEM is determined appropriately depending on the culture vessel. A volume substantially equal to the volume of the medium that is added in conventional culture may be considered appropriate. An excess of the methylcellulose-containing DMEM will cause no problem except that it takes time to be degraded with an enzyme. A shortage of the methylcellulose-containing DMEM will cause several troubles such as a further increase in viscosity due to evaporation of water or the aggregate touching the bottom of culture equipment. If the droplets of the infusion injected into the medium assume a spherical shape, it is highly likely that the aggregate formed also assumes a spherical shape. The injected cells become aggregated in about 10 minutes. The resultant cells are cultured as such in the methylcellulose-containing medium in a $CO_2$ incubator at 33-37° C. for 24 hours to 7 days until a polymer-loaded cell or cell aggregate is obtained. It is important that the concentration of a polymer in cell suspension be lower than the concentration of a swellable material in the medium. If the concentration difference between the polymer and the swellable material is large, the medium absorbs the moisture content of the polymer part and swells to thereby concentrate the polymer. When encapsulation is intended, the polymer in the cell suspension is preferably at a concentration that enables gelation of the polymer (approximately 3-4 mg/ml for collagen and 9-12 mg/ml for Matrigel™, though the exact value varies from one commercial product to another).

When the polymer is to be loaded between cell tissues, its concentration in the cell suspension is preferably approx. 0.1 mg/ml for collagen and approx. 0.3-0.4 mg/ml for Matrigel™. A lower concentration may also be selected depending on the purpose. As shown in the Example described later, compared to 3D cell tissues composed of cells alone prepared in Matrigel™-free medium, 3D cell tissues prepared with Matrigel™ stock solution (9-12 mg/ml) contain cells as dispersed in gel capsules. On the other hand, when Matrigel™ is diluted to 0.3-0.4 mg/ml, the tissue image obtained is almost the same as that of the image from the cell alone state.

For collecting the polymer-loaded cell or cell aggregate, the viscosity of the methylcellulose-containing medium may be reduced by degrading methylcellulose with cellulase because said medium would otherwise have such a high viscosity that collecting operations are difficult to perform. Even in the case of using a swellable material other than methylcellulose, treatments for reducing the viscosity of a swellable material-containing medium are preferably carried out (e.g., treatment with a degrading enzyme, change toward lower temperatures, slight pH change, etc.). Degrading enzymes that decompose cell-constituting components are cytotoxic and therefore undesirable. As regards methylcellulose, its skeleton (cellulose) is degraded with cellulase. Cellulose is a component of plant cells but absent from human cells. Cellulase would, therefore, have little toxicity.

According to the method of the present invention, a polymer-loaded cell or cell aggregate is obtained. By culturing the resultant cell aggregate as such, it is possible to form a 3D tissue. The property and/or the function of this 3D tissue may be improved relative to the property and/or the function of cells that have not formed a 3D tissue or the property and/or the function of a 3D tissue that has been formed without loading a polymer between cells. Therefore, the present invention provides a method for controlling the property and/or the function of a cell or a cell aggregate, comprising culturing the polymer-loaded cell or cell aggregate prepared by adding a solution containing a polymer and at least one cell to a medium containing a swellable material to thereby aggregate the polymer together with the cell.

In the method of the present invention, the polymer-loaded cell or cell aggregate may take the form of a polymer capsule filled with a cell or a cell aggregate. For example, it is possible to introduce into the polymer capsule one to several small tissue units such as pancreatic islets. In the encapsulation of pancreatic islets, alginate gel is used for the purpose of immunosuppression. By using ECM gel instead of alginate gel, a further function may be added.

Further, according to the method of the present invention, it becomes possible to prepare cell-containing ECM gel capsules in an oil-free manner. When gel capsules are prepared by this method, cells are not damaged by oil components and can be cultured in ECM gel capsules. Therefore, the present invention provides a method for culturing a cell or a cell aggregate, comprising: preparing a polymer capsule filled with a cell or a cell aggregate by adding a solution containing a polymer and at least one cell to a medium containing a swellable material to thereby aggregate the polymer together with the cell; and culturing the cell or cell aggregate within the capsule. For example, cells, such as primary cultured neurons, that do not have very high proliferative capacity but will die in conventional two-dimensional culture may be suitable for culture within this capsule (culture does not necessarily involve proliferation). Even with proliferative cells, some may successfully proliferate in the capsule by producing an enzyme that degrades ECM. Further, an approach to expand cells within a space created in capsules is also possible. For example, cells or cell aggregates are embedded in alginate gel and then encapsulated with ECM gel. For information, alginic acid can be gelated by being added dropwise to a container of calcium chloride (to form the so-called artificial salmon roe). The resultant double-walled capsule consisting of alginate gel and ECM gel is treated with an enzyme, alginate lyase, to selectively digest the alginate gel. This enzyme does not digest ECM gel. Therefore, according to this method, it is possible to prepare hollow ECM capsules and to expand cells in the inner space thus provided. With this method, even cells that proliferate to a certain extent do not break the capsule for a limited period of time.

Those polymer capsules filled with a cell or a cell aggregate that have been prepared by the method of the present invention may be aligned by means of a 3D bioprinter. For example, those cell aggregates loaded with a low concentration of polymer (e.g., EMC) (which may be such that they have formed 3D cell tissues) may further be encapsulated with a high concentration of polymer (e.g., ECM) and the resultant capsules may then be aligned by means of a 3D bioprinter. Therefore, in the method of the present invention, at least one cell contained in a solution to be added to a medium containing a swellable material may be a polymer-loaded cell or cell aggregate prepared by the method of the present invention.

EXAMPLES

Hereinbelow, the present invention will be described in more detail with reference to the following Examples.

Example 1

[Outline of the Technique of the Present Invention]

In cell assays or regenerative medicine using cells, it is believed that three-dimensional (3D) organization of those cells is an effective means to enhance the differentiation potential of the cells. However, in order to prepare still higher value-added 3D tissues that are needed in drug screening or regenerative medicine, a more elaborate technique for constructing 3D tissues is demanded. For example, since organs existing in human bodies are made of cells and extracellular matrixes (ECMs) laminated in layers, positive use of ECM is believed to be effective for improving the function of 3D organs.

The subject technique relates to a method for preparing cell-containing ECM gel capsules in an oil-free manner, as well as a method for mixing a water-soluble polymer (such as ECM or dextran) into the inside of cell aggregates at a desired concentration. The subject technique provides a method for adding various values to 3D cell tissues by controlling the property and the function thereof.

[Advantage of the Subject Technique]

In the preparation of 3D cell tissues, a method using U-bottom 96-well plates or the hanging-drop method is conventionally used. It is possible to mix ECM into the inside of cell tissues by these methods but in contrast with 3D cell tissues which are formed as a result of the gathering of cells at the bottoms of U-bottom plates or liquid drops, ECM which is soluble is present uniformly in liquid culture media. Therefore, the most part of ECM is unable to contribute to cell aggregation. In the method using a U-bottom 96-well plate, 100 µl of liquid culture medium is used; even in the hanging drop method, 20 µl is used. The volume occupied by 2000 cells (i.e., a cell count generally used in the preparation of aggregates) is approx. 8.4 nanoliters when the cell diameter is taken as 20 µm. Theoretically, this means that ECM is only mixed in 3D cell tissues at an efficiency of approx. 8.4 nl/100 µl=$\frac{1}{12000}$ or 8.4 nl/20 µl=$\frac{1}{2400}$. On the other hand, in the present invention, 2000 cells are mixed with 1 µl of ECM-containing medium so that ECM and the cells are allowed to aggregate simultaneously, which makes it possible for the most part of ECM to contribute to 3D cell tissues efficiently (FIG. 1). For this reason, the cost of ECM can be reduced to about several thousand to ten thousand times less. Besides, according to the present invention, it is possible to efficiently use artificial ECM that cannot be synthesized in a large quantity or rare ECM that can only be extracted in an extremely small quantity for such a reason that the source is a small organism.

[Methods and Materials]

Cells

A human hepatoma cell line Hep G2 was used. Cells were cultured in Dulbecco's Modified Eagle Medium (DMEM containing 10% fetal bovine serum and antibiotics) and passaged in a subconfluent state.

ECM and High Molecular Weight Polysaccharides

Matrigel™ (Matrigel Matrix Growth Factor Reduced, 354230, BD Bioscience), FITC-labeled collagen (4001, Chondrex) and FITC-labeled dextran (FD250S, Sigma-Aldrich) were used. Matrigel™ was used either in stock solution or in dilution with a cooled medium. FITC-labeled collagen was first returned to neutrality in pH and then was diluted with a cooled medium before use. Both Matrigel™ and collagen were passed through a 40 µm strainer before use to remove the fraction that had gelled unexpectedly. FITC-labeled dextran was treated with a medium to prepare a 1.25 mg/ml solution which was d then diluted 1/100 before use.

Preparation of ECM Gel Capsules and 3D Cell Tissues Loaded with Water-Soluble Polymer A 2 ml aliquot of methylcellulose (MC) medium prepared by dispersing MC in DMEM at a concentration of 3% was poured into a 35 mm petri dish which was then left stationary for a while to remove air bubbles and flatten the liquid surface. Water-soluble polymers such as ECM and polysaccharides were either used in stock solution or optionally diluted with a medium, and Hep G2 cells were then suspended to give a cell density of $2\times10^7$ cells/ml. ECM-containing samples were handled with special care (e.g., keeping on ice) so that no gelation would occur due to a rise in temperature. The resultant suspension of cells and ECM was injected into the MC medium with a micropipette in 1 µl portions at appropriate intervals. With a 35 mm petri dish, it is possible to form about 100 capsules or 3D cell tissues. The injected water-soluble polymer and cells became aggregated in about 10-30 minutes. The cells were cultured as such in the MC medium for 1-2 days. In the case of a gelatable polymer such as ECM, gel capsules were formed when the polymer concentration was high and cell aggregates were formed when it was low. For collecting these capsules or aggregates from the MC medium, the viscosity of the MC medium was reduced by degrading MC with cellulase because otherwise the medium would have a high viscosity.

Calculation of Cross Sectional Areas of ECM Gel Capsules and 3D Cell Tissues

One day after injection of a cell suspension into MC medium, 3D cell tissues were observed with a phase contrast microscope. Cross sectional areas of 5 aggregates per one condition were calculated to determine mean value and standard deviation.

Observation of 3D Cell Tissues with Confocal Microscope

When FITC-labeled collagen or FITC-labeled dextran was used, cells were pre-stained with PKH26 (Sigma-Aldrich). The collected ECM gel capsules and 3D cell tissues were observed with a confocal microscope (Leica).

Hematoxylin-Eosin (HE) Staining

After washing with phosphate-buffered saline (PBS), the ECM gel capsules and 3D cell tissues collected from MC medium were fixed with 4% paraformaldehyde at room temperature for 15 minutes. A small amount of 1% alginic acid solution containing about 50 aggregates was gelated by addition of 10% calcium chloride solution. The resultant gel was embedded in paraffin to prepare sections. Sliced samples were hydrophilized and then subjected to HE staining.

Albumin Secretion Assay

After being collected from MC medium, the 3D cell tissues were poured into a 6-well plate at a density of about 10 tissues/well together with 2 ml of fresh medium and cultured for 24 hours. Albumin concentrations in the medium before and after the culture were measured with an ELISA kit. The 3D cell tissues were collected separately to quantify DNA levels. Then, albumin secretion activities per unit DNA level and per unit time were determined. Each experiment was performed with three samples (n=3), followed by calculation of mean and standard deviation.

Ammonia Reduction Assay

After being collected from MC medium, the 3D cell tissues were poured into a 6-well plate at a density of about 30 tissues/well together with 2 ml of a medium to which ammonium chloride had been added at a concentration of 2 mM and the cells were then cultured for 6 hours. Ammonia concentrations in the medium before and after the culture were measured with Ammonia Test Wako. The 3D cell tissues were collected separately to quantify DNA levels. Then, albumin secretion activities per unit DNA and per unit time were determined. Each experiment was performed with three samples (n=3), followed by calculation of mean and standard deviation.

Gel Capsulation with Oil and Cytotoxicity Test

A 2 ml aliquot of mineral oil (M8410, Sigma-Aldrich) was poured into a 35 mm petri dish. Hep G2 cells were suspended in Matrigel™ stock solution to give a cell density of $2 \times 10^7$ cells/ml. The cell-suspending Matrigel™ solution was handled with special care (e.g., keeping on ice) so that gelation would not occur due to a temperature rise. This cell-suspending Matrigel™ solution was injected into the mineral oil with a micropipette in 1 µl portions at appropriate intervals and gelated in a $CO_2$ incubator to thereby prepare gel capsules filled with cells. Gel capsules were prepared in the same manner except that cell-suspending Matrigel™ solution was injected into MC medium instead of mineral oil. After incubation in mineral oil or MC medium for 30 minutes, capsules were taken out and washed. Then, Live/Dead Assay (Life Technologies) was performed. In this assay, viable cells emit green fluorescence and dead cells red fluorescence. When all the cells are killed with 4% formaldehyde, every nucleus emits red fluorescence, so a numerical value obtained by dividing the red fluorescence occupied area by the total area of 3D cell tissues was taken as a dead cell ratio of 100%; and dead cell ratios inside the capsules prepared with mineral oil or MC medium were determined.

Observation of the Microstructures of 3D Cell Tissues with Transmission Electron Microscope 3D Cell tissues (at day 2 of culture) were fixed with 3% glutaraldehyde and 1% osmium tetroxide in this order. Subsequently, the 3D cell tissues were dehydrated and embedded in epoxy resin. The resultant resin block was sliced with an ultra-microtome to prepare samples, which were observed with a transmission electron microscope.

Statistical Analysis t-Tests were performed and differences were judged significant at $p<0.05$.

[Results and Discussion]

Aggregation Phenomenon of Cells and ECM when MC Medium was Used

We have already reported a technique for efficiently aggregating cells using MC medium[1]. Specifically, when approx. 1 µl of conventional medium is injected into MC medium together with cells or particulate substances, MC medium absorbs the conventional medium and swells. As a result, the cells or particulate substances become aggregated in about 10-30 minutes. MC medium has a capacity of aggregating even polystyrene particles with a diameter of approx. 100 nm. However, it was unknown whether water-soluble polymers such as ECM could be aggregated without diffusing in MC medium. Then, the inventor performed an experiment in which cells were suspended in a fluorescence-labeled type I collagen solution (which had its pH adjusted to neutrality on ice to be in such a state that it would gel when heated to 37° C.), followed by injection into a cooled MC medium. The volume of injection was 1 µl, and the concentration was adjusted to such a density that approx. 2000 Hep G2 cells would be contained. As shown in FIG. 1, it was revealed that not only red fluorescence-labeled cells but also green fluorescence-labeled ECM components were aggregated with the passage of time, enabling the formation of 3D cell tissues composed of cells and ECM.

Figure 2:
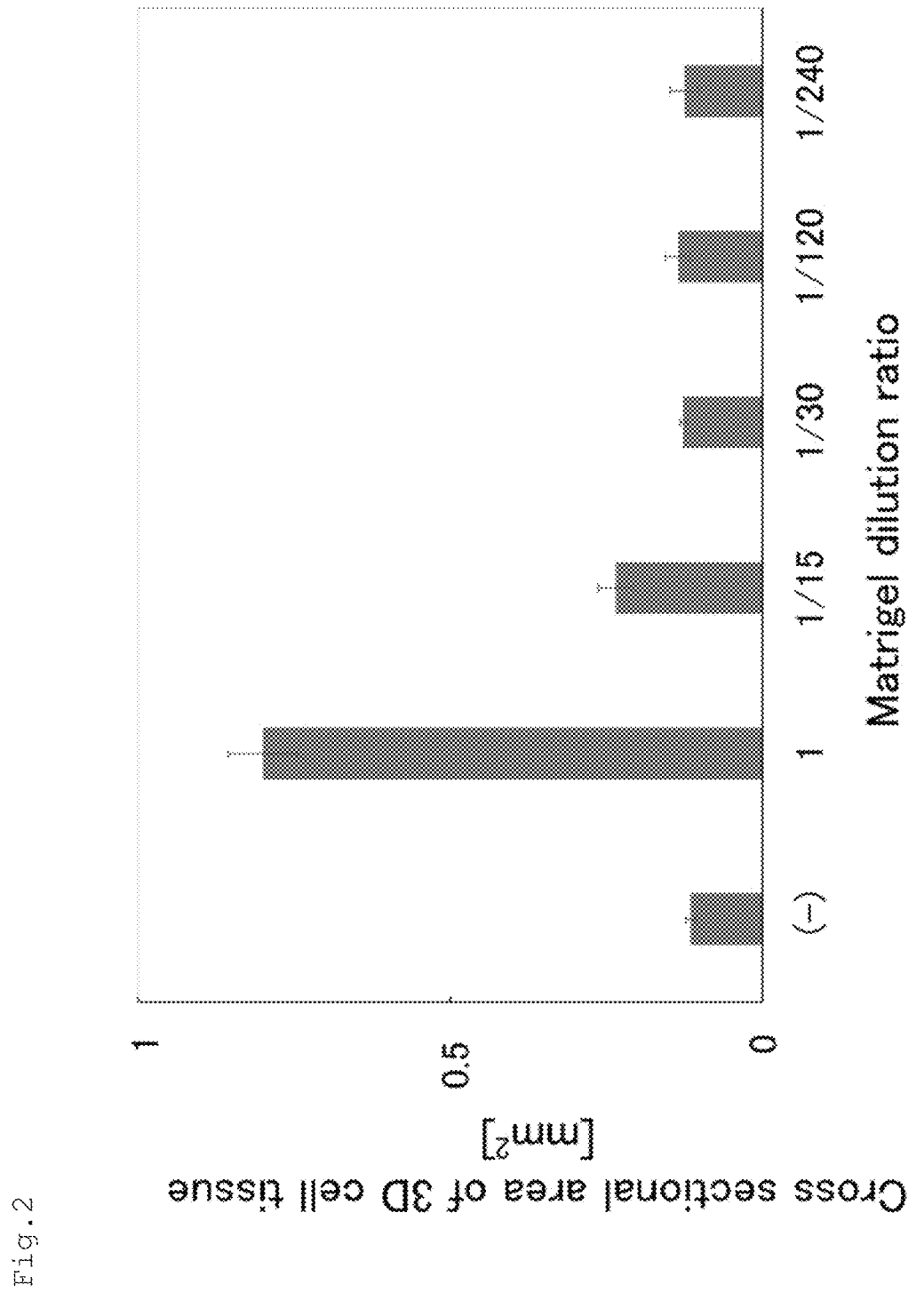
FIG. 2 shows the cross-sectional area of a tissue that varies with the dilution ratio of gel.

It is expected with type I collagen and Matrigel™ that depending on their concentration, the aggregation speed may slow down in the process and that they will gel to form gel capsules. Then, the inventor serially diluted Matrigel™ in the state of a commercial product (stock solution) with a medium to prepare a 1 µl solution containing 2000 Hep G2 cells, followed by its injection into MC medium. One day after that, mean value of the cross sectional areas of 3D cell tissues was calculated with a phase contrast microscope; the mean was approx. 0.8 $mm^2$ when Matrigel™ stock solution was used, whereas it was approx. 0.1 $mm^2$ when cells were used alone (FIG. 2). As Matrigel™ was diluted, the cross sectional area was shown to decrease gradually, becoming almost equal to that of cell alone 3D tissue when the dilution ratio was 1/30 (FIG. 2). In the case of collagen, it has also been found that when the concentration is high, the cross sectional area of 3D cell tissue increases to form gel capsules whereas when the dilution ratio is approx. 1/40, the cross sectional area becomes almost equal to that of cell alone 3D tissue.

Figure 3:
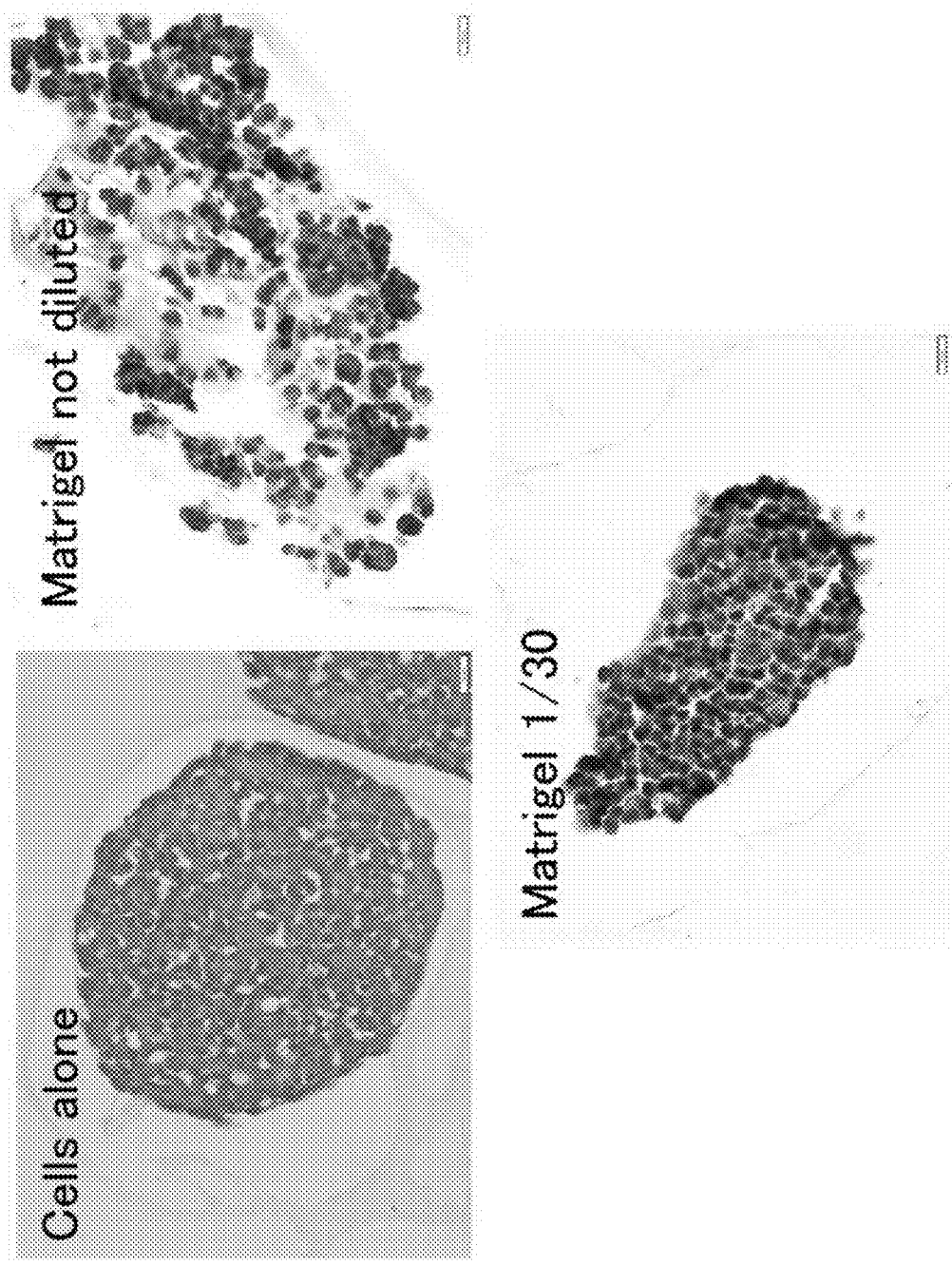
FIG. 3 shows the dependency of the internal structure of 3D cell tissues on the dilution ratio of gel.

In order to further investigate the fact that either gel capsules or cell-based tissues are formed depending on the concentration of Matrigel™, the present inventor prepared paraffin sections of 3D cell tissues and subjected them to hematoxylin-eosin staining (FIG. 3). It was found that compared to the cell alone 3D cell tissues prepared with Matrigel™-free medium, the use of Matrigel™ stock solution resulted in the formation of gel capsules having cells dispersed therein. On the other hand, when Matrigel™ was diluted at 1/30, a tissue image almost identical to that of cell alone 3D tissue was obtained.

Figure 4:
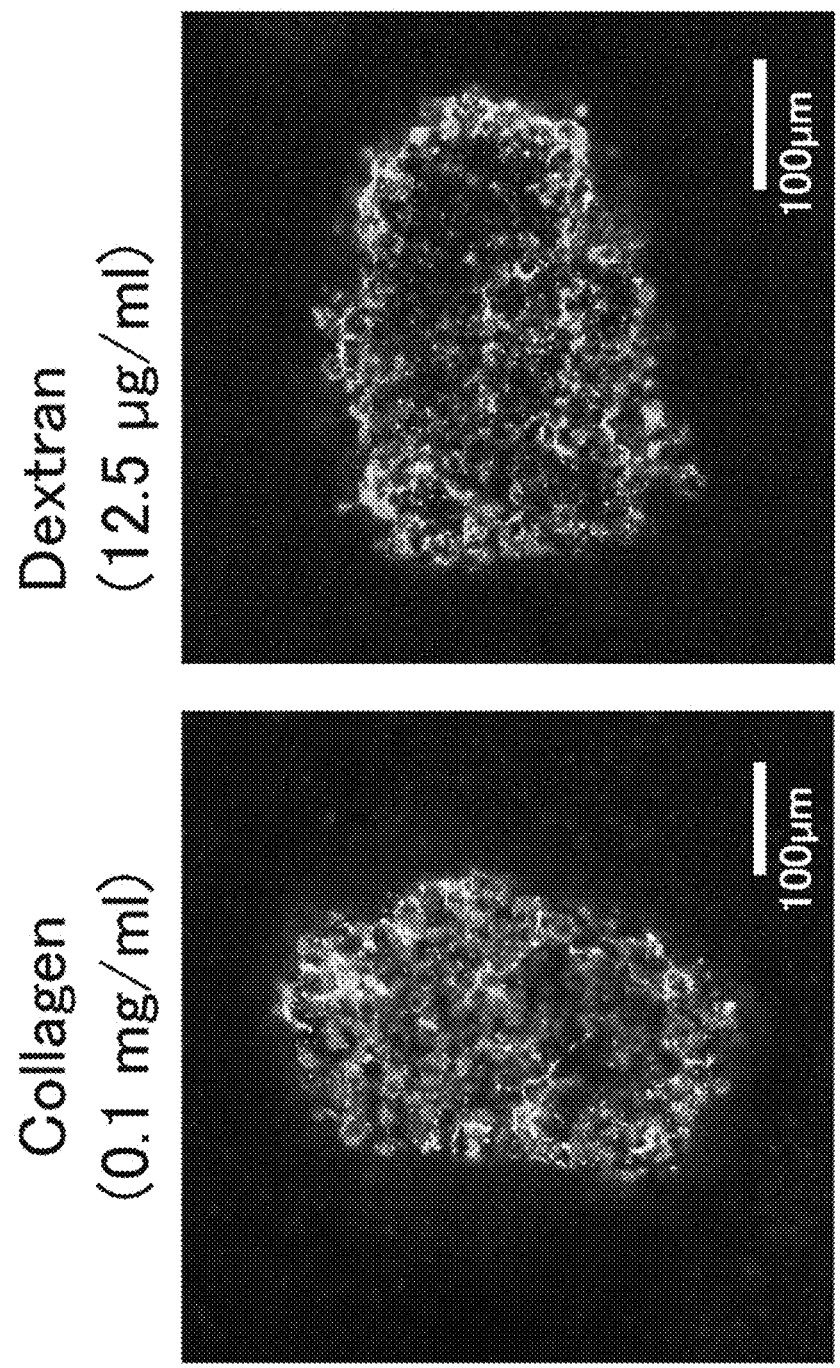
FIG. 4 shows FITC-labeled collagen and FITC-labeled dextran that were loaded between cells inside of 3D tissues.

At the dilution ratio of 1/30 for Matrigel™ and 1/40 for collagen, the resultant 3D cell tissues have a size almost equal to that of cell alone 3D tissues. In order to examine whether ECM remains inside of such 3D cell tissues, 3D cell tissues were prepared with fluorescence-labeled collagen and the inside of the resultant tissues was observed with a confocal microscope. As a result, it was revealed that collagen at the dilution ratio of 1/40 (approx. 0.1 mg/ml) was loaded between cells in such a manner that it formed a network structure. Further, similar to ECM, fluorescence-labeled dextran (approx. 12.5 μl/mg) could be loaded between cells of 3D cell tissues, so it became clear that not only protein polymers such as Matrigel™ or collagen but also polysaccharide polymers such as dextran can be handled by the subject technique (FIG. 4). Since water-soluble protein polymers and polysaccharide polymers can be concentrated without diffusion by MC medium, it is expected that the subject technique will have the effect with other water-soluble polymers.

Figure 5:
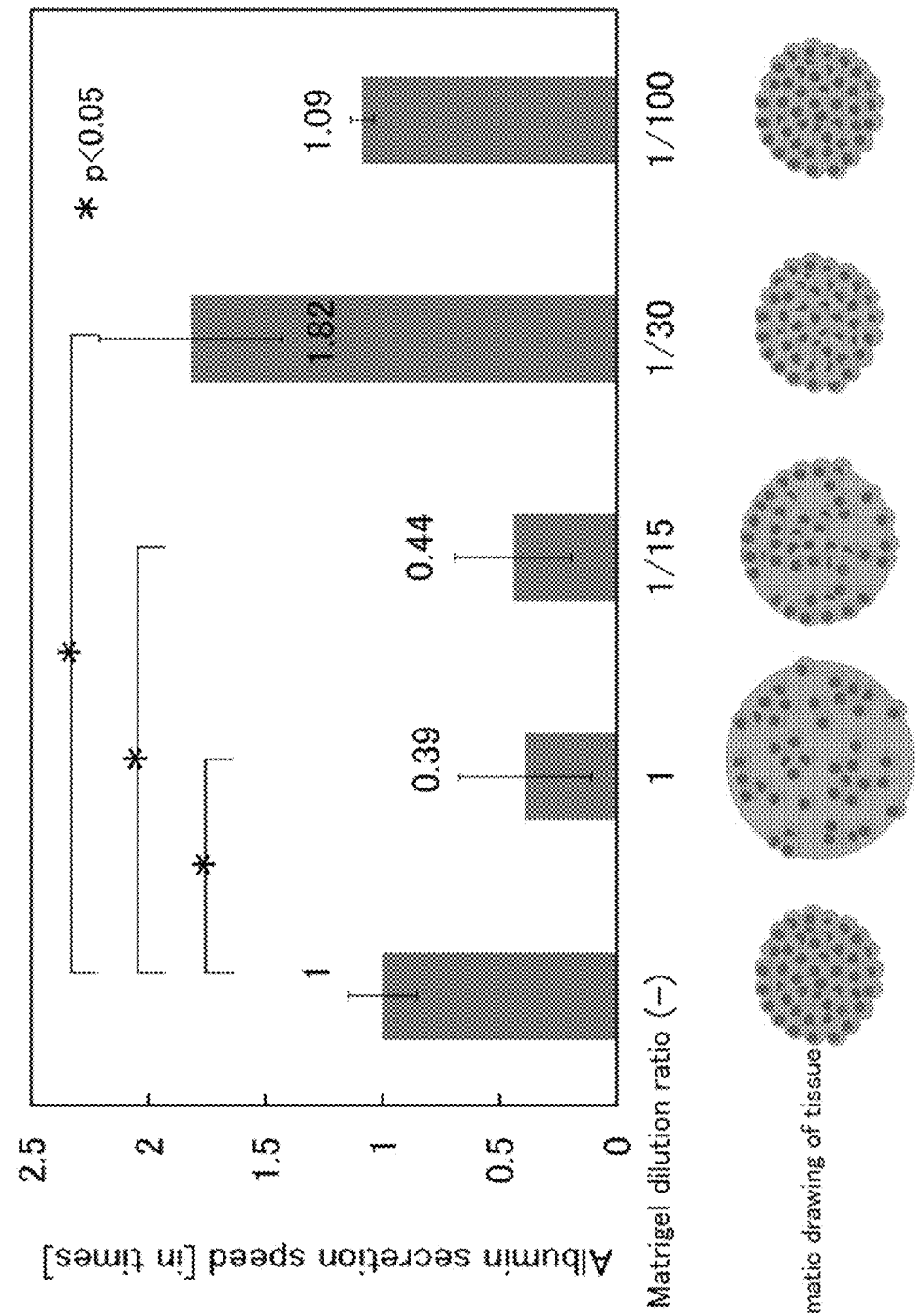
FIG. 5 shows changes in albumin secretion activity with the dilution ratio of gel.
Figure 6:
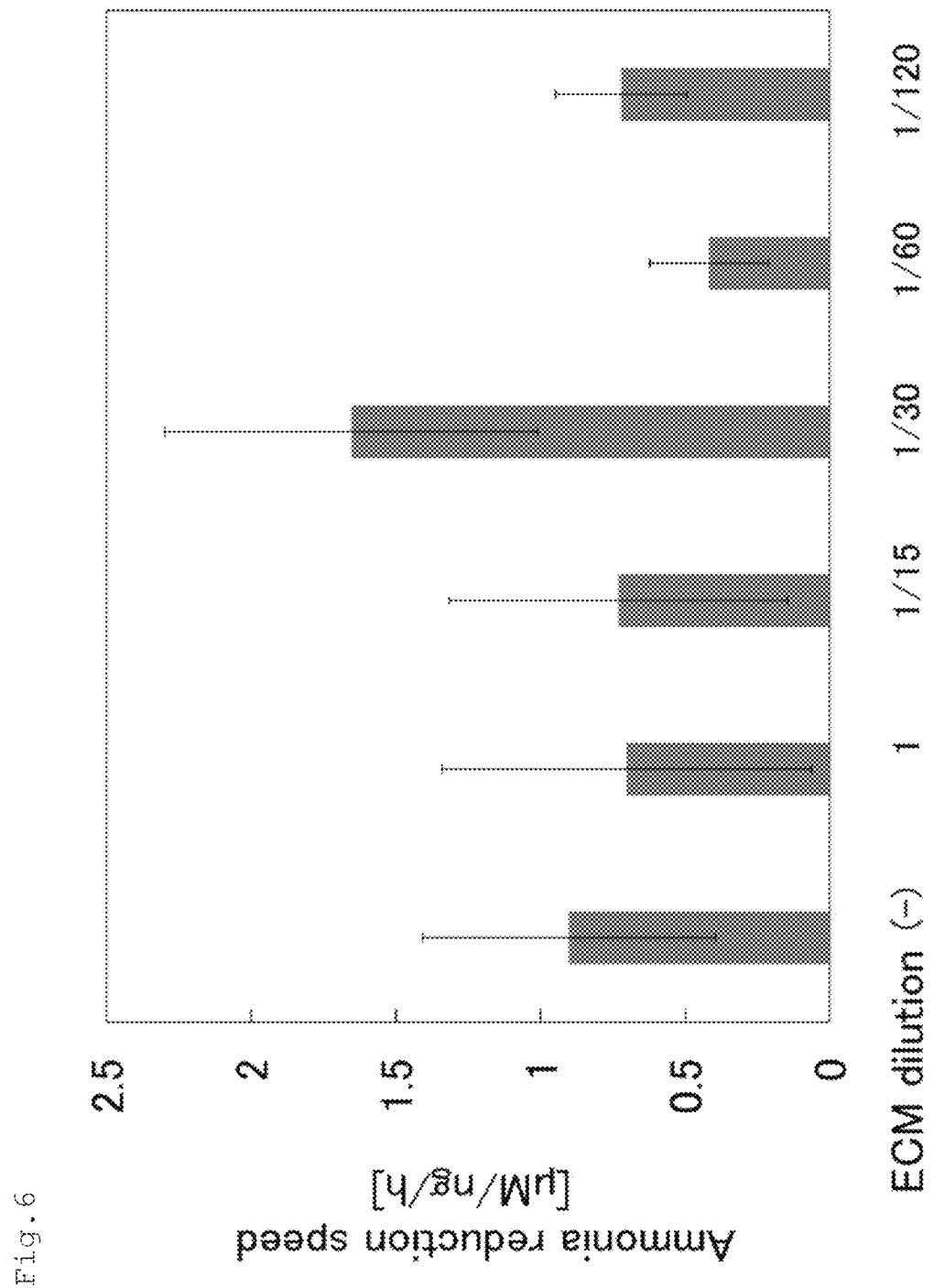
FIG. 6 shows changes in ammonia reduction activity with the dilution ratio of gel.

By using the present invention, encapsulation of cells with ECM, loading of water-soluble polymers such as ECM or polysaccharides into cell aggregates, and other operations are performed. As a result, implementation of cell cultures or eliciting of cell functions that has been impossible in conventional methods can be realized. As one example, the present inventor used Matrigel™ to examine conditions that would enhance the hepatic function of Hep G2 cells. FIG. 5 shows the results of comparison of albumin secretion activities in 3D cell tissues prepared using Matrigel™ as stock solution or Matrigel™ diluted with medium. Under conditions where Matrigel™ concentration was relatively high, i.e., conditions for forming Matrigel™ capsules, the cells were found to separate from each other, showing a lower albumin secretion activity than the control (cells alone, without Matrigel™) Interestingly, it was found that when Matrigel™ was progressively thinned, the albumin secretion activity became higher than that of the control at the dilution ratio of 1/30. This effect disappeared when Matrigel™ was further diluted. From these results, the present inventor predicted the following: for the albumin secretion activity of Hep G2 cells, it is critical that the cells adhere or come very close to each other and albumin secretion activity is low in a capsule state where Matrigel™ is abundantly present around cells; when Matrigel™ is present thinly between cells that are nearly close enough to adhere to each other, t not only the cell-to-cell effect but also the cell-to-Matrigel™ effect develops to show a higher albumin secretion activity than the control.

The effect caused by the difference in Matrigel™ dilution ratio on ammonia reduction activity in Hep G2 cells was examined in the same manner as on albumin secretion activity. As a result, a tendency similar to that seen in albumin secretion activity was observed. It was shown that the function of Hep G2 cells can be enhanced by aggregating them in a liquid culture medium containing Matrigel™ as diluted to approx. 1/30. From these results, it is easily anticipated that they will be reversed under conditions that require the cell density to be retained at low level. Although the dilution ratio and the type of gel need be optimized since they would vary for an individual cell type, 3D cell tissues superior in various functions may potentially be prepared by using the present invention.

Figure 7:
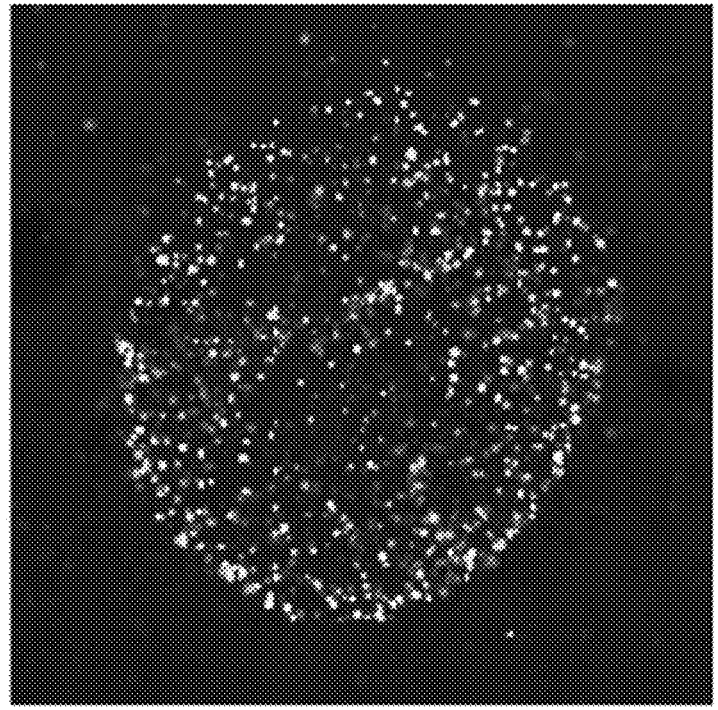
FIG. 7 shows comparison of cytotoxicity depending on the method of encapsulation.
Figure 7:
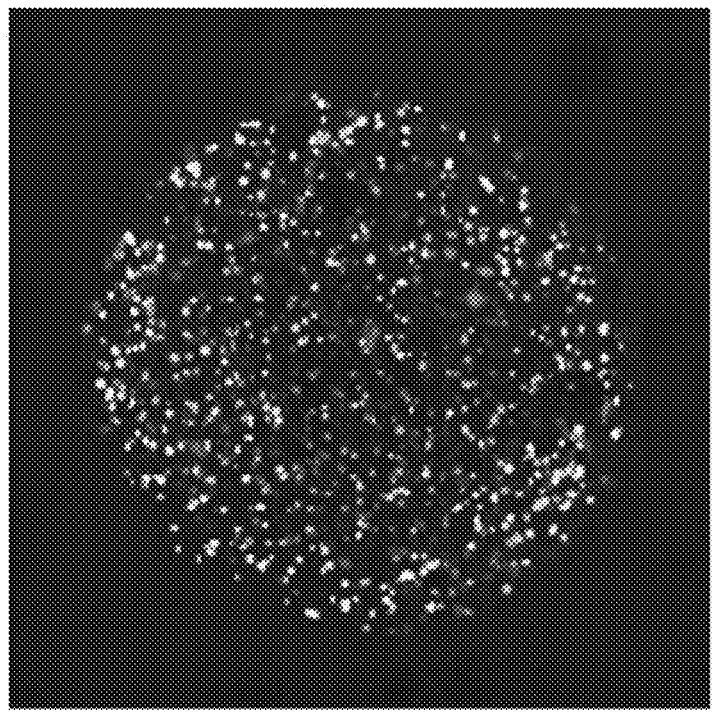
Figure 8:
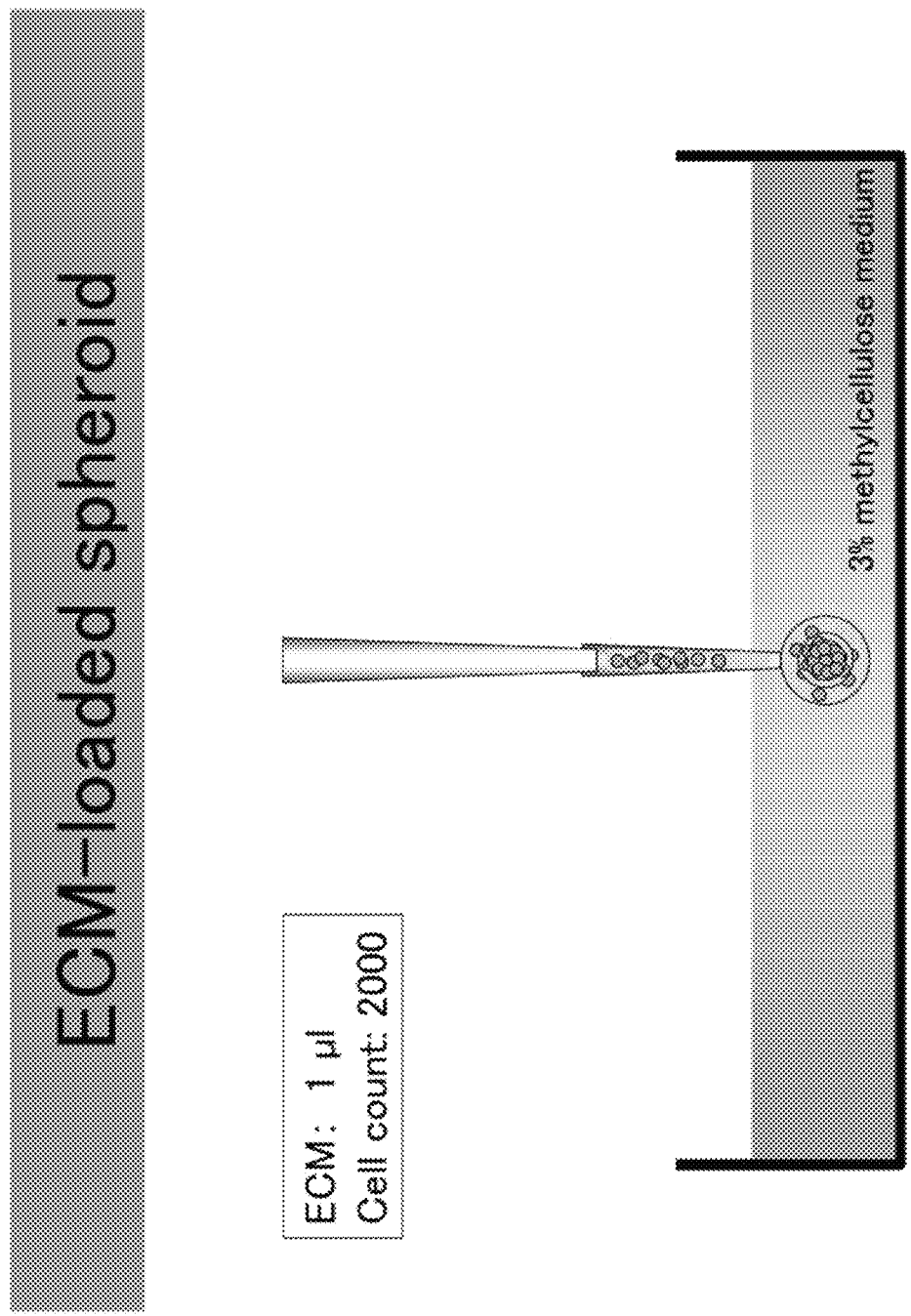
FIG. 8 schematically shows one embodiment of preparation of polymer-loaded cell aggregates according to the method of the present invention. Methylcellulose was used as a swellable material, and ECM was used as a polymer to be loaded between cells.
Figure 9:
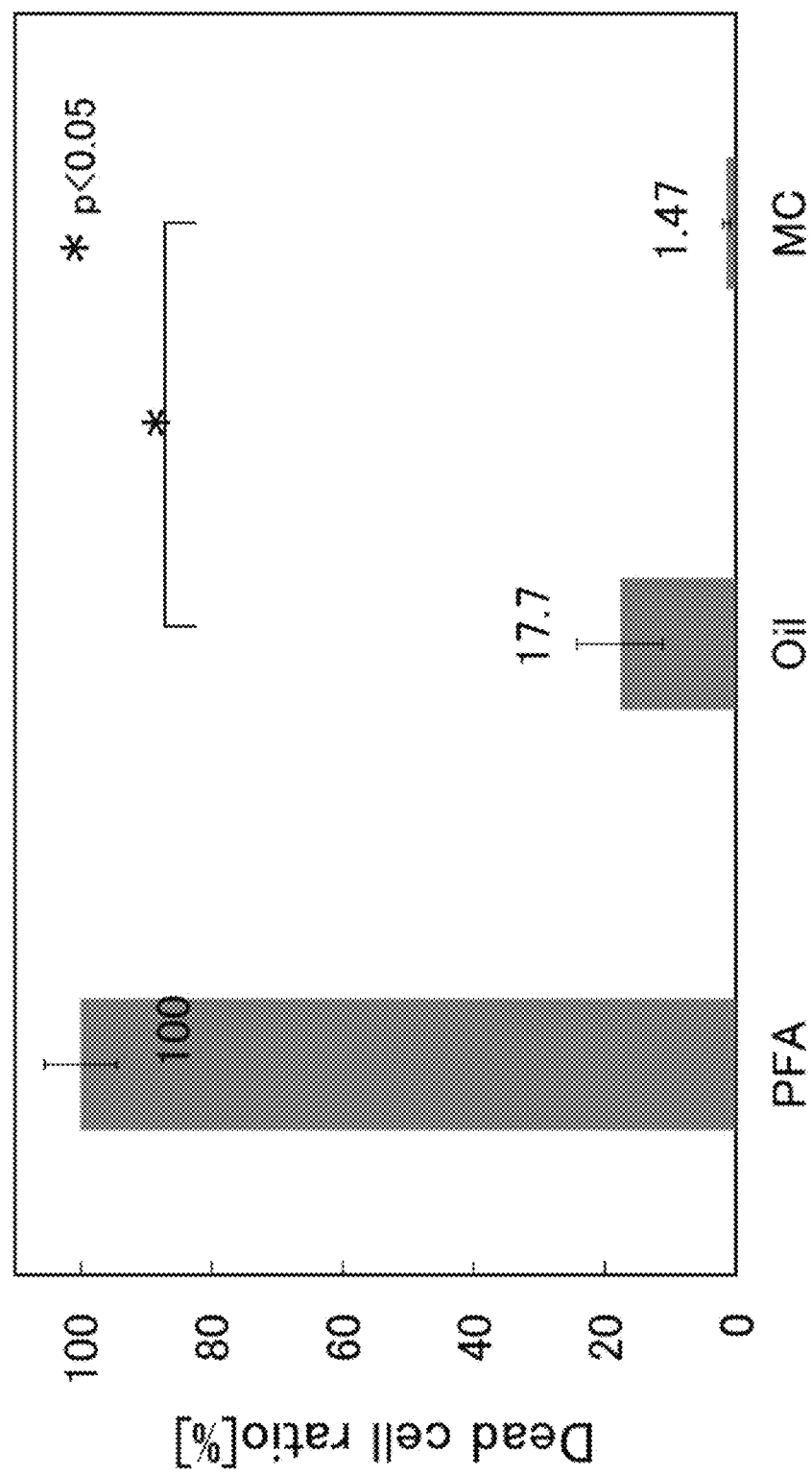
FIG. 9 shows quantitative evaluation of cytotoxicity depending on the method of capsulation. All cells in capsules prepared with MC medium were killed with paraformaldehyde, and with such cells (PFA) taken as a reference (100%), the dead cell ratios of cells under different conditions (cells in capsules prepared with mineral oil (Oil) or MC medium (MC)) were calculated.

ECM gel encapsulation by the oil-based conventional method and encapsulation using MC medium were compared for toxicity to the encapsulated cells. Briefly, gel capsules were prepared by suspending Hep G2 cells were suspended in Matrigel™ stock solution and 1 μl of the resultant cell suspension was injected into a mineral oil (a product after validation by a mouse embryo culture test), followed by culturing in a $CO_2$ incubator for 30 minutes. Subsequently, the resultant capsules were collected and washed. The viability of cells was checked using Live/Dead reagent. As it turned out, a certain amount of red dead cells were observed in the capsules prepared in the mineral oil but such dead cells were hardly observed in the capsules prepared with the MC medium (FIG. 7). When quantitative evaluation was performed, a significant difference was observed between the encapsulation using the mineral oil and the encapsulation using the MC medium (FIG. 9). The mineral oil purchased for the present experiment is prepared for the purpose of culturing mouse embryos and contains no cytotoxic compounds. However, cell death presumably attributable to the mineral oil was observed, suggesting that cell survival ratio might be reduced in the presence of an operation that causes an oil to cell contact. Encapsulation using the MC medium which can prevent such cell death has been found to offer a great advantage.

When the 3D cell tissues composed of Hep G2 cells alone and the 3D cell tissues aggregated together with 1/30 dilution of Matrigel™ were compared for their internal structure, it turned out that structures with developed microvilli (presumably bile canaliculi) were observed frequently in the Matrigel™-loaded 3D cell tissues. This result demonstrates that by loading 3D cell tissues with ECM efficiently, the tissue structures can be brought even closer to the real organs.

CONCLUSION

It has become clear that water-soluble polysaccharides such as ECM or dextran are unable to diffuse in a solution of a different species of polymer such as MC; and that when they have a large difference in concentration (i.e., the concentration of ECM or dextrin is low and that of MC is high), the MC solution absorbs the moisture content of the ECM or dextrin part and swells to thereby concentrate ECM or dextrin. The method for preparing gel capsules and 3D cell tissues containing ECM or the like according to this technique is capable of using ECM more efficiently than conventional methods, with the additional advantage that the effect as of oil upon cells can be ignored. Actually, enhancement of albumin secretion activity and reassembly of bile canalicular structures have been confirmed. The technique described herein will predictably become an essential tool for realizing in vitro preparation of tissues provided with high function and microstructures.

REFERENCE

1. Kojima, N., Takeuchi, S. and Sakai, Y. Rapid aggregation of heterogeneous cells and multiple-sized microspheres in methylcellulose medium. Biomaterials, 33, 4508-4514 (2012)

All publications, patents and patent applications cited herein are incorporated herein by reference in their entirety.

INDUSTRIAL APPLICABILITY

The present invention is applicable to drug discovery (drug screening using cell functions as an indicator), human-on-a-chip (human organs are embedded in a small device to perform various assays as on interactions between organs), regenerative medicine (organization of iPS cell-derived various differentiated cells) and so forth.

The invention claimed is:
1. A method for preparing water-soluble polymer-loaded cells or cell aggregate, comprising:
adding a cell suspension containing a water-soluble polymer and cells suspended therein to a medium contain- ing a swellable material to aggregate the water-soluble polymer together with the cells by the swelling of the swellable material to form said water-soluble polymer-loaded cells or cell aggregate, wherein the concentration of the water-soluble polymer in the cell suspension is lower than the concentration of the swellable material in the medium.

2. The method of claim 1, wherein the cell aggregate forms a three-dimensional (3D) tissue.

3. The method of claim 2, wherein the property and/or the function of the 3D tissue is improved relative to the property and/or the function of cells that have not formed a 3D tissue or the property and/or the function of a 3D tissue that has been formed without loading a water-soluble polymer between cells.

4. The method of any one of claims 1 to 3, wherein the water-soluble polymer-loaded cells or cell aggregate comprises a water-soluble polymer capsule filled with cells or a cell aggregate.

5. A method for preparing water-soluble polymer-loaded cells or cell aggregate, comprising:
adding a cell or cell aggregate suspension containing a water-soluble polymer and cells or cell aggregates therein to a medium containing a swellable material to aggregate the water-soluble polymer together with the cells or cell aggregates by the swelling of the swellable material to form said water-soluble polymer-loaded cells or cell aggregates, wherein the cell or cell aggregate suspension to be added to the medium containing a swellable material comprises the water-soluble polymer-loaded cells or cell aggregates prepared by the method of claim 1.

6. A method for controlling the property and/or the function of a cell or a cell aggregate, comprising culturing the water-soluble polymer-loaded cell or cell aggregate prepared by the method of claim 1 or 5.

7. A method for culturing cells or a cell aggregate(s), comprising:
preparing a water-soluble polymer capsule filled with cells or a cell aggregate by adding a cell suspension containing a water-soluble polymer and cells to a medium containing a swellable material to aggregate the water-soluble polymer together with the cells by the swelling of the swellable material, wherein the concentration of the water-soluble polymer in the cell suspension is lower than the concentration of the swellable material in the medium; and
culturing the cells or cell aggregate within the capsule.

8. The method of claim 1, 5 or 7, wherein the swellable material is methylcellulose.

9. The method of claim 1, 5 or 7, wherein the swellable material is methylcellulose and the concentration of the methylcellulose in the medium is 1-3% by mass.

10. The method of claim 1, 5 or 7, wherein the water-soluble polymer is selected from the group consisting of collagen, proteoglycans, hyaluronic acid, laminin, tenascin, entactin, elastin, fibrillin, fibronectin, dextran, starch, glycogen, cellulose, alginic acid and collagen-denatured gelatin.

* * * * *